United States Patent [19]

Caufield

[11] Patent Number: 5,066,671
[45] Date of Patent: Nov. 19, 1991

[54] ELLAGIC ACID DERIVATIVES AS PHOSPHOLIPASE A₂ INHIBITORS

[75] Inventor: Craig E. Caufield, Middlesex, N.J.

[73] Assignee: American Home Products Corporation, New York, N.Y.

[21] Appl. No.: 552,659

[22] Filed: Jul. 16, 1990

[51] Int. Cl.⁵ .............................................. A61K 31/35
[52] U.S. Cl. ................................................... 514/453
[58] Field of Search ......................................... 514/453

[56] References Cited

U.S. PATENT DOCUMENTS 3,576,007 4/1971 Hochstein ........................ 260/343.2
3,694,557 9/1972 Persinos ........................... 260/343.2

OTHER PUBLICATIONS

Beilstein, vol. 19, p. 285, 2d Ed.
Beilstein, vol. 19, p. 3164, 3/4 Ed.
Derwent Publications: 66-33545F.
Derwent Publications: 78-88538A.

Primary Examiner—Stanley J. Friedman
Attorney, Agent, or Firm—George Tarnowski

[57] ABSTRACT

There are disclosed a method for the treatment or prevention of immunoinflammatory conditions by administering to a mammal an effective amount of a compound having the formula:

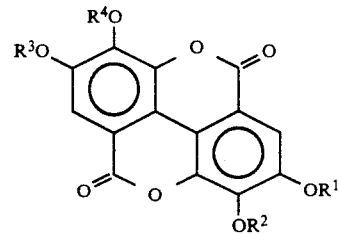

wherein
$R^1$, $R^2$, $R^3$, and $R^4$ are each, independently, hydrogen, alkyl, aralkyl, aryl, or

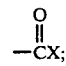

X is alkyl, aryl, or -NR⁵R⁶;
$R^5$ and $R^6$ are each independently hydrogen, alkyl, or aryl; aryl is

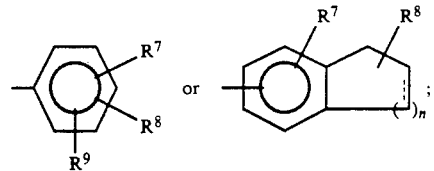

where the dotted line represents an optional double bond;
$R^7$, and $R^8$ and $R^9$ are each, independently, hydrogen, alkyl, hydroxy, alkoxy, carbalkoxy, halo, nitro, amino, cyano, trifluoromethyl, or a carboxylic acid;
n=1-3;
or a pharmaceutically acceptable salt thereof.

3 Claims, No Drawings

ELLAGIC ACID DERIVATIVES AS PHOSPHOLIPASE $A_2$ INHIBITORS

BACKGROUND OF THE INVENTION

The present invention is directed to ellagic acid and certain derivations which are useful as anti-inflammatory and antiallergic agents by virtue of their ability to inhibit phospholipase $A_2$.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287-299 (1984)]. This is through their vasodepressor activities, participation in pain and fever, augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Back et al., *J. Immun.*, 215, 115-118 (1980); *Biochem. Biophys. Res. Commun.*, 93, 1121-1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484-486 (1980) and Piper, *Int. Arch. Appl. Immunol.*, 76, suppl. 1, 43 (1985)] which stimulates the release of mucus from airways in vitro [Marom et al., *Am. Rev. Resp. Dis.*, 126, 449 (1982)], are potent vasodilators in skin [see Bisgaard et al., *Prostaglandins*, 23, 797 (1982)], and produce a wheal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831-833 (1981)], which stimulates cell accumulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 19, 87 (1986).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products: (1) free AA which is then available for subsequent metabolism by either the cyclooxygenase or lipoxygenase enzymes, and (2) lysophospholipid. When alkylarachidonoyl-glycerophosphatidylcholine is acted upon by the $PLA_2$ the generation of platelet activating factor (PAF) is initiated; PAF is pro-inflammatory in its own right [see Wedmore et al., *Br. J. Pharmacol.*, 74, 916-917 (1981)]. In this regard it may be noted that the anti-inflammatory steroids are thought to inhibit eicosanoid synthesis by inducing the synthesis of a $PLA_2$ inhibitory protein denominated macrocortin, lipomodulin or lipocortin [see Flower et al., *Nature*, London, 278, 456 (1979) and Hirata et al., *Proc. Natn. Acad. Sci. U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Thromb. Res.*, 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

Ellagic acid (4, 4', 5, 5', 6, 6'-hexahydrodiphenic acid 2, 6, 2', 6'-dilactone), I, is a naturally occurring substance which has been obtained from guava, rasberries, walnuts, and cloves (see, U.S. Pat. No. 3,576,007).

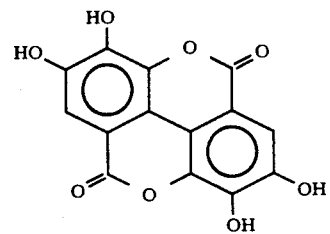

I

The isolation and synthesis of ellagic acid and its ether and ester derivatives are well known in the prior art (see, Beilstein Vol. 19, p. 285, 2nd Ed. and Vol. 19, p. 3164, ¾ Ed.)

Ellagic acid, its derivatives, and salts thereof have been shown to be useful as hemostatic agents [see, Derwent Publications 82-88884OE, 66-40347F, 66-33545F and U.S. Pat. No. 3,576,007) by virtue of their ability to activate Hageman factor (Ratnoff et al., J. Lab. Clin. Med. 63, 359 (1964)]. In addition, 3,3'dimethyl ellagic acid has been shown to possess antitumor activity (Derwent Publications 78-88538A).

DESCRIPTION OF THE INVENTION

This invention provides anti-inflammatory and antiallergic agents of the formula

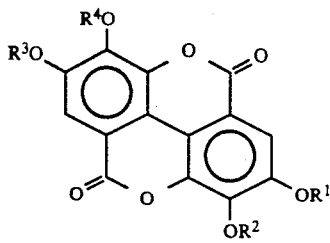

wherein
$R^1$, $R^2$, $R^3$, and $R^4$ are each, independently, hydrogen, alkyl of 1-9 carbon atoms, aralkyl of 7-10 carbon atoms, aryl, or

X is alkyl of 1-6 carbon atoms, aryl, or $-NR^5R^6$;
$R^5$ and $R^6$ are each independently hydrogen, alkyl of 1-6 carbon atoms, or aryl; aryl is

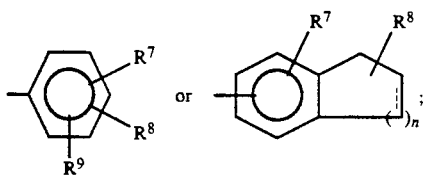

where the dotted line represents an optional double bond;
$R^7$, $R^8$ and $R^9$ are each, independently, hydrogen, alkyl of 1-6 carbon atoms, hydroxy, alkoxy of 1-6 carbon atoms, carbalkoxy of 2-7 carbon atoms, halo, nitro, amino, cyano, trifluoromethyl, or a carboxylic acid; n=1-3;
or a pharmaceutically acceptable salt thereof.

Of those compounds, the preferred members are ellagic acid ($R^1$, $R^2$, $R^3$, and $R^4$ are hydrogen) and those where $R^1$, $R^2$, $R^3$, and $R^4$ are each, independently, hydrogen, or

where X is alkyl of 1-9 carbons.

The starting materials used in the preparation of the compounds of the invention are commercially available or can be prepared by conventional procedures taught in the chemical literature.

The pharmaceutically acceptable salts may be formed from organic bases such as alkanolamines, and other mono-, di-, and tri-substituted amines, and inorganic cations such as sodium, potassium, and the like.

The compounds of the invention, by virtue of their ability to inhibit activity of $PLA_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; immunoinflammatory disorders, such as contact dermatitis, irritable bowel disease and the like; and various inflammatory conditions such as those present in rheumatoid arthritis, osteoarthritis, tendinitis, bursitis, psoriasis (and related skin inflammations) and the like.

When the compounds within the scope of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tabletdisintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The $PLA_2$ inhibitory and anti-inflammatory activity of the compounds of the invention, may be demonstrated by standard pharmacological procedures which are described more fully in the examples given hereinafter.

These procedures, inter alia, deermine the specificity of action of the compounds of the invention as $PLA_2$ inhibitors as measured by their ability to inhibit the synthesis of $LTB_4$ and $TxB_2$ by rat glycogen-elicited polymorphonuclear leukocytes, as well as measure their ability to inhibit arachidonic acid release mediated by human source $PLA_2$. The procedures further measure the ability of the compounds of the invention to inhibit, in vivo, the activity of exogenously administered $PLA_2$ and the ability to inhibit the acute inflammatory response caused by the administration of carrageenan. The results of the in vivo assays demonstrated that the compounds of this invention had a high degree of specificity as PLA$_2$ inhibitors. This specificity is evidenced by the effective inhibition of PLA$_2$ mediated release of arachidonic acid with little effect on the synthesis of LTB$_4$ and TxB$_2$, which are indicators of lipoxygenase and cyclooxygenase activities, respectively. The compounds of this invention also were effective in preventing inflammatory response in vivo to both PLA$_2$ and carrageenan challenges.

The following examples show the preparation and pharmacological testing of representative compounds within the invention.

EXAMPLE 1

Ellagic Acid

Ellagic acid was obtained from Aldrich Chemical Company, Milwaukee, WI and used without further purification.

EXAMPLE 2

Ellagic Acid Tetraacetate

To a slurry of 10.0 g (29.6 mmol) of ellagic acid dihydrate in 250 mL of pyridine was added 100 mL of acetic anhydride. The solution was heated to reflux for 3 hours. The hot solution was filtered and upon cooling, crystals formed. The crystals were filtered, washed with hexane, and vacuum dried to give 1.28 g (9.2%) of pure ellagic acid tetraacetate.

$^1$H NMR (CDCl$_3$, 400 MHz) $\delta$8.75 (s,2H, aromatic), 2.46 (s, 6H, CH$_3$CO$_2$Ar), 2.39 (s, 6H, CH$_3$CO$_2$); IR (KBr) 3120 (CH), 1810 (C=O), 1770 (C=O), 1635, 1601, 1490, 1430, 1400, 1365, 1340, 1240, 1200, 1155, 1115, 1080, 1025, 945, 930, 900, 830, 810 cm$^{-1}$; MS (pos. ion FAB) 471 (M+H), 451, 429, 217, 181, 131, 109, 91 (100), 73,57.

Analysis Calc'd. for C$_{22}$H$_{14}$O$_{12}$: C, 56.18; H, 3.00; N, 0.00. Found: C, 55.89; H, 3.01; N, 0.17.

EXAMPLE 3

Ellagic Acid Diacetate

To a solution of 1.00 g of ellagic acid tetraacetate in 5 mL of refluxing pyridine was added 2.5 mL of water. The solution was brought back to reflux and a precipitate formed after 4 minutes. The heat was removed and 15 mL of water was added. The precipitate was filtered, washed with methanol, and washed with acetone. The solid was recrystallized from dimethylformamide to give 400 mg of pure ellagic acid diacetate.

$^1$H NMR (d$_6$-DMSO, 400 MHz) $\delta$7.85 (s, 2H, aromatic, 2.34 (s, 6H, CH$_3$CO$_2$Ar); IR (KBr) 3450 (OH), 3100 (CH), 1775 (C=O), 1740 (C=O), 1610, 1499, 1430, 1350, 1285, 1210, 1180, 1105, 1050, 1005, 930, 880, 820 cm$^{-1}$; MS (pos. ion FAB) 387 (M+H), 345, 257, 229, 194, 159, 117, 91, 85, 81, 73, 71, 69 (100).

Analysis Calc'd. for C$_{18}$H$_{10}$O$_{10}$: C, 55.97; H, 2.61; N, 0.00. Found: C, 55.65; H, 2.50; N, 0.08.

EXAMPLE 4

The compounds 5- and 12-hydroxyeicosatetraenoic acid (5-HETE and 12-HETE) and LTB$_4$ are early arachidonic acid oxidation products in the lipoxygenase cascade, which have been shown to mediate several aspects of inflammatory and allergic response. This is especially true with respect to 5,12-diHETE, which is also denoted as LTB$_4$ [see Ford-Hitchinson, *J. Roy. Soc. Med.*, 74, 831 (1981)]. Compounds which inhibit the PLA$_2$-mediated release of arachidonic acid thereby effectively prevent the oxidation of arachidonic acid to the various leukotriene products via the lipoxygenase cascade. Accordingly, the specificity of action of PLA$_2$ inhibitors can be determined by the activity of test compounds in this assay, which measures the ability of compounds to inhibit the synthesis of LTB$_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150-200 g) which receive an injection of 6% glycogen (10 ml i.p.). Rats are sacrificed 18-24 hours post injection by CO$_2$ asphyxiation and the elicited cells are harvested by peritoneal lavage using physiological saline (0.9% NaCl). The exudate is centrifuged at 400 xg for 10 minutes. The supernatant fluid is discarded and the cell pellet is resuspended to a concentration of 2.0×10$^7$ cells/mL in HBSS containing Ca$^{++}$ and Mg$^{++}$ and 10 $\mu$M L-cysteine.

To 1 mL aliquots of cell suspension, test drugs or vehicle are added, then preincubated at 37° C. for 10 minutes. A23187 (1 $\mu$M), [$^3$H]-AA (3.0 $\mu$Ci/mL) and unlabeled AA (1 $\mu$M) are then added and the samples are further incubated for 10 minutes. The reaction is terminated by centrifugation and pelleting cells. Supernatants are then analyzed by HPLC analysis on a 15 cm×4.6 mm ID supelcosil LC-18 (Supelco)(3M) column, using a two solvent system at a flow rate of 1.4 mL total flow as follows:

Solvent A: 70:30 17.4 mM H$_3$PO$_4$:CH$_3$CN
Solvent B. CH$_3$CN

Gradient: (system is equilibrated with Solvent A)

| Time | Percent A | Percent B |
|------|-----------|-----------|
| 0    | 100       | 0         |
| 15.0 | 100       | 0         |
| 20.0 | 65        | 35        |
| 40.0 | 65        | 35        |
| 42.0 | 10        | 90        |
| 50.0 | 10        | 90        |
| 50.1 | 100       | 0         |

Percent solvent changes are accomplished in a linear fashion.

Injections: 140 $\mu$L of each supernatant is injected directly onto column and $^3$H arachidonic acid metabolites are monitored using an on-line radioactivity detector (Ramona, IN/US, Fairfield, NJ).

Standards: 10$^4$ – 2.0×10$^4$ dpm of eicosanoids of interest are injected in 90 $\mu$L EtOH cocktail.

Co-chromatography with standard [$^3$H] leukotriene B$_4$ (LTB$_4$) in medium of stimulated PMN exposed to drug is compared to that found in medium of stimulated cells exposed to no drug, generating percent inhibition.

Results are expressed as percent inhibition at a given compound dose.

Testing compounds of the invention in this assay gave the following results:

TABLE I

| Compound  | % Inhibition     |
|-----------|------------------|
| Example 1 | 39 (at 10 $\mu$M) |
| Example 2 | −31 (at 10 $\mu$M) |

TABLE I-continued

| Compound | % Inhibition |
| --- | --- |
| Example 3 | + |

+Not evaluated.

EXAMPLE 5

The procedure of Example 4 is also employed for the determination of the extent to which compounds of the invention inhibit the synthesis of the arachidonic acid cyclooxygenase oxidation product $TxB_2$.

In this assay, the procedure of Example 1 is carried out as described. However, in order to determine cyclooxygenase activity, the samples are cochromatographed with authentic reference $[^3H]$-$TxB_2$.

The results are calculated as in Example 1 and presented below:

TABLE II

| Compound | % Inhibition |
| --- | --- |
| Example 1 | 4 (at 10 μM) |
| Example 2 | + |
| Example 3 | 9 (at 10 μM) |

+Not evaluated.

EXAMPLE 6

The compounds of the invention are tested in an in vitro isolated phospholipase $A_2$ assay to determine the ability of the test compounds to inhibit the release of arachidonic acid from an arachidonic acid-containing substrate by the action of phospholipase $A_2$ enzyme from human and non-human sources.

This assay is carried out as follows:

Into a 15 mL polypropylene tube are added the following:

| Agent | Volume, μL | Final Conc. |
| --- | --- | --- |
| $^3$H-AA E.coli substrate[1] | 25 | 5 nmoles PL |
| $CaCl_2(0.1M)$[2] | 5 | 5 mM |
| Tris-HCl(0.5M)pH7.5[3] | 20 | 100 mM |
| Water[4] | 25 | |
| Drug/vehicle[5] | 1 | 50 μM |
| $PLA_2$ | 25 | Volume yielding 12% |
| | 100 | hydrolysis in 10 min. |

*pre-incubate at room temperature 30 min prior to substrate addition.
[1]Prepared by adding 2 mL deionized and distilled water to 2 mL $^3$H-arachidonate labeled E. coli (lower count), to which is added 1 mL of $^3$H-arachidonate labeled E. coli (higher count) to yield a total of 5 m substrate (containing 1000 nmoles phospholipid).
[2]Stock 0.1 m $CaCl_2$, required for enzyme activity.
[3]Stock 0.5 m Trisma-Base.
Stock 0.5 M Trisma-HCl. Adjust pH to 7.5 (optimum for enzyme).
[4]Deionized and distilled water.
[5]Stock 10 mM prepared in dimethyl sulfoxide. Make 1:2 dilution with dimethyl sulfoxide and add 1 μL to 100 μL assay tube.
[6]Two human $PLA_2$ enzymes are used: (a) Semi-purified human platelet acid extract $PLA_2$ (in 10 mM sodium acetate buffer, pH 4.5). Remove protein precipitate by centrifugation at about 2200 rpm for 10 minutes. (b) Purified human synovial fluid.

Incubate the 100 μL reaction mixture for 10 minutes at 37° C. in a shaking water bath. The reaction is terminated by the addition of 2 mL tetrahydrofuran, followed by vortexing. $NH_2$ columns (100 μg/mL-Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by β-counting analysis. A "total counts" sample is prepared by pipetting 25 μL $^3$H-arachidonate E. coli directly into a scintillation vial to which is added 1 mL tetrahydrofuran. 10 mL aquasol (scintillation cocktail) is added to all samples.

Calculations:

$$\% \text{ hydrolysis} = \frac{[^3H]AA \text{ dpm (sample)} - [^3H]AA \text{ dpm (nonspecific hydrolysis)}}{\text{total counts } dpm} \times 100$$

$$\% \text{ change} = \frac{\text{vehicle } dpm - \text{drug } dpm}{\text{vehicle } dpm} \times 100$$

| Activity of Standard Drugs: | | |
| --- | --- | --- |
| | $IC_{50}$ (μM) | |
| Drug | Human Platelet $PLA_2$ | Human Synovial $PLA_2$ |
| Arachidonic Acid | 8.6 | 3.2 |
| Monoalide | 25.2 | 0.14 |

When tested in this assay, the compounds of the invention gave the following results:

TABLE III

| | % Inhibition at 10 μM | | $IC_{50}$ (μM) | |
| --- | --- | --- | --- | --- |
| Compound | HP* | HSF** | HP | HSF |
| Example 1 | 38.8+ | 86.5+, 89.5+ | — | 0.021 |
| Example 2 | −16.6 | 90.7 | — | — |
| Example 3 | 0 | 95.6 | — | 0.360 |

*human platelet
**human synovial fluid
+at 50 μM

EXAMPLE 7

The ability of the compounds of the invention to inhibit paw edema induced by the exogenous administration of $PLA_2$ is measured in the in vivo $PLA_2$ murine paw edema assay.

The assay is carried out as follows:

Non-fasted, male CD-1 mice (8 weeks old; 31–36 grams) are placed in plastic boxes in groups of six. The right hind paw volume is measured using mercury plethysmography (zero time). Compounds are dosed orally (0.5 mL of 0.5% Tween80) 1 or 3 hours prior to $PLA_2$ injection or intravenously (0.2 mL in 0.3% dimethylsulfoxide/saline) 3 minutes prior to $PLA_2$ injection. A solution of purified $PLA_2$, from the diamond back cotton mouth snake (A. piscivorus piscivorus) is prepared in saline at a concentration of 6 μg/mL. Fifty (50) μL (0.3 μg) of this $PLA_2$ solution is injected subcutaneously into the right hind paw with a plastic 1 mL plastic syringe (27 gauge, 1" needle). Paw volume of the injected paw is measured again at 10 minutes, 30 minutes and 60 minutes after $PLA_2$ injection. Animals are euthanized with $CO_2$ at the completion of the study.

The paw edema is calculated by subtracting the zero time volume from the volume recorded at each time period. Mean paw edema for each treatment group is then calculated and expressed as (μL±S.E.). Drug effects are expressed as a percent change from control (vehicle) values. Statistical significance is determined by a oneway analysis of variance with LSD comparison to control ($p<0.05$). $ED_{50}$'s are determined using repression analysis.

The activity of standard drugs in this assay is as follows:

| Compound | ED$_{50}$ mg/kg p.o. at +10 min. |
| --- | --- |
| Cyproheptadine | 3.1 |
| BW755C | 50 |
| Dexamethasone* | 10 |
| Naproxen | 18 |
| Aristolochic Acid** | Not Active |
| Luffarrellolide** | Not Active |

*p.o. - 3 hr.
**Some activity (30% inhibition) only when co-injected with enzyme.

When tested in this assay, a compound of the invention gave the following results:

TABLE IV

| Compound | Dose mg/kg | % Change in Edema | | |
| --- | --- | --- | --- | --- |
| | | 10 min | 30 min | 60 min |
| Example 1 | 10 (i.v.)* | −22 | −64 | −18 |
| | 100 (p.o.)** | −35 | +4 | −73 |
| Example 2+ | | | | |
| Example 3+ | | | | |

*intravenous
**peroral
+not evaluated

The results show that the tested compound is effective in vivo in inhibiting edema induced by the exogenous administration of snake venom PLA$_2$.

EXAMPLE 8

The compounds of the invention are tested in the rat carrageenan paw edema assay to determine their ability to inhibit the acute inflammatory response.

This assay is carried out as follows:

140-180 gm male Sprague-Dawley rats, in groups of 6 animals, are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral ED$_{50}$ (95%) C.L.) mg/kg |
| --- | --- |
| Indomethacin | 3.7 (0.6, 23.8) |
| Aspirin | 145.4 (33.1, 645.6) |
| Phenylbutazone | 26.2 (2.3, 291.0) |

When tested in this assay, a compound of the invention gave the following results, demonstrating activity in the rat carrageenan paw edema assay:

TABLE V

| Compound | % Inhibition at 50 mg/kg (peroral) |
| --- | --- |
| Example 1 | 37 |
| Example 2 | + |
| Example 3 | + |

+Not evaluated.

What is claimed is:

1. A method of preventing or treating immunoinflammatory conditions in a mammal in need thereof by administering an immunoinflammatory amount of a compound having the formula

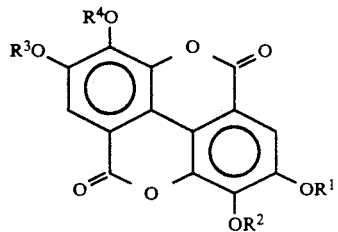

wherein
R$^1$, R$^2$, R$^3$, and R$^4$ are each, independently, hydroge, alkyl of 1-9 carbon atoms, aralkyl of 7-10 carbon atoms, aryl, or

X is alkyl of 1-6 carbon atoms, aryl, or —NR$^5$R$^6$;
R$^5$ and R$^6$ are each independently hydrogen, alkyl of 1-6 carbon atoms, or aryl; aryl is

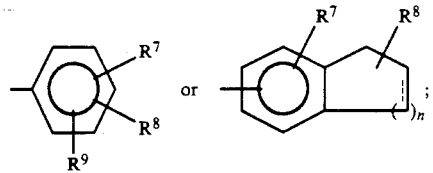

where the dotted line represents an optional double bond;
R$^7$, R$^8$ and R$^9$ are each, independently, hydrogen, alkyl of 1-6 carbon atoms, hydroxy, alkoxy of 1-6 carbon atoms, carbalkoxy of 2-7 carbon atoms, halo, nitro, amino, cyano, trifluoromethyl, or a carboxylic acid;
n = 1-3;
or a pharmaceutically acceptable salt thereof.

2. A method as claimed in claim 1 where R$^1$, R$^2$, R$^3$, and R$^4$ are hydrogen.

3. A method as claimed in claim 1 where R$^1$, R$^2$, R$^3$, and R$^4$ are each, independently, hydrogen or

where X is alkyl of 1-9 carbon atoms.

* * * * *